(12) United States Patent
Sutcliffe

(10) Patent No.: US 6,190,413 B1
(45) Date of Patent: Feb. 20, 2001

(54) VERTEBRAL IMPLANT

(75) Inventor: John Sutcliffe, Good Easter (GB)

(73) Assignee: Ulrich GmbH & Co. KG, Ulm (DE)

( * ) Notice: Under 35 U.S.C. 154(b), the term of this patent shall be extended for 0 days.

(21) Appl. No.: 09/293,943

(22) Filed: Apr. 16, 1999

(30) Foreign Application Priority Data

Apr. 16, 1998 (DE) .............................. 198 16 782

(51) Int. Cl.$^7$ .............................. A61F 2/44; A61B 17/70
(52) U.S. Cl. .......................................... 623/17.11; 606/61
(58) Field of Search ................. 623/17; 606/61, 606/63, 90

(56) References Cited

U.S. PATENT DOCUMENTS

| 4,386,603 | * | 6/1983 | Mayfield | 606/105 |
|---|---|---|---|---|
| 4,657,550 | * | 4/1987 | Daher | 623/17 |
| 5,171,278 | * | 12/1992 | Pisharodi | 623/17 |
| 5,336,223 | * | 8/1994 | Rogers | 606/61 |
| 5,387,239 | * | 2/1995 | Bianco et al. | 623/18 |
| 5,390,683 | * | 2/1995 | Pisharodi | 128/898 |
| 5,397,363 | * | 3/1995 | Gelbard | 623/17 |
| 5,458,641 | * | 10/1995 | Rimenez | 623/17 |
| 5,571,192 | * | 11/1996 | Schonhoffer | 623/17 |
| 5,658,335 | * | 8/1997 | Allen | 623/17 |
| 5,702,453 | * | 12/1997 | Rabbe et al. | 623/17 |
| 5,702,455 | * | 12/1997 | Sagger | 623/17 |
| 5,776,197 | * | 7/1998 | Rabbe et al. | 623/17 |
| 5,776,198 | * | 7/1998 | Rabbe et al. | 623/17 |
| 5,860,977 | * | 1/1999 | Zucherman et al. | 606/61 |
| 5,865,846 | * | 2/1999 | Bryan et al. | 623/17 |
| 5,916,267 | * | 6/1999 | Tienboon | 623/17 |
| 5,989,290 | * | 11/1999 | Biedermann et al. | 623/17 |
| 6,001,130 | * | 12/1999 | Bryan et al. | 623/17 |

FOREIGN PATENT DOCUMENTS

| 3729600 | 3/1989 | (DE) . |  |
|---|---|---|---|
| 4423257 | 1/1996 | (DE) . |  |
| 2718635 | 10/1995 | (FR) . |  |
| WO 94/07441 | * 9/1994 | (WO) | 623/17 |

* cited by examiner

Primary Examiner—Gene Mancene
Assistant Examiner—Michael B. Priddy
(74) Attorney, Agent, or Firm—Herbert Dubno; Andrew Wilford

(57) ABSTRACT

An implant for insertion between a pair of spaced vertebrae has a center element and a pair of end elements fitted to the center element and each adapted to engage a respective one of the vertebrae. The center and end elements have formations for varying the spacing between the end elements. Respective brackets fixed to the end elements are each fixable to the respective vertebra. The formations include screwthreads engaged between the center and end elements and the end elements are formed as caps engaged over ends of the center element. Each bracket is generally L-shaped and has a long leg attached to the respective vertebrae and an arcuate short leg attached to the respective element.

8 Claims, 8 Drawing Sheets

VERTEBRAL IMPLANT

FIELD OF THE INVENTION

The present invention relates to vertebral implant. More particularly this invention concerns such an implant positioned between two vertebrae, normally in the place of a removed vertebra or intervertebral disk.

BACKGROUND OF THE INVENTION

When a vertebra is broken or crushed it is frequently necessary to ablate the body of the crushed or broken vertebra or vertebrae. In order, however, to prevent the spinal column from collapsing with damage to the fragile spinal cord running in the vertebral foramen forward of the vertebral body, it is necessary to employ an implanted spacer. This device is braced vertically between the bodies of the adjacent vertebra and holds them apart at the desired spacing. It may even serve to distract two vertebrae which have become too closely spaced due to crushing of a vertebra or disk.

In U.S. Pat. No. 5,571,192 a spinal implant is described for engagement in a space left by ablation of a vertebral body between a pair of adjacent vertebrae. It has a tubular center element extending along an axis and a pair of end elements. The center element is formed with upper and lower screwthreads of opposite hand and with a plurality of radially throughgoing apertures. The upper and lower tubular end elements are each formed with a plurality of radially throughgoing apertures, each have a circular-section inner end threaded onto a respective one of the screwthreads, and each have an outer end adapted to bear on a respective one of the adjacent vertebrae.

Thus such an implant can be set in an area where the body or bodies or one or more vertebra have been ablated. The length of the implant is then increased by rotating the center element to force out the end elements and bring their outer ends into solid engagement with the confronting vertebral surfaces. The screwthreads offer sufficient mechanical advantage so that the system can even be used to distract the vertebrae, as is frequently necessary in the event of a crushing injury. The tubular elements of the implant can be filled with bone cement and/or bone fragments to ensure that the implant becomes anchored in place in living bone. Since the outer elements surround the screwthreads of the inner element, once installed the screwthreads will be largely covered so that their sharp edges do not impair healing.

Such an arrangement serves very well to maintain the axial spacing between the vertebrae it is installed between, but must normally be used in conjunction with a separate bone plate and or external dorsal appliance secured by bone screws to the flanking vertebrae. This extra equipment is needed to prevent any relative lateral shifting of the vertebrae and to prevent the implant from moving out of position.

Not only is the plate or appliance difficult to install, but it is extremely inconvenient for the patient whose wound must often be left open. In addition the plate or appliance often block access to the implant so if same needs to be adjusted, for instance lengthened, it must be removed and reinstalled.

OBJECTS OF THE INVENTION

It is therefore an object of the present invention to provide an improved intervertebral implant.

Another object is the provision of such an improved intervertebral implant which overcomes the above-given disadvantages, that is which eliminates the need for substantial additional hardware.

SUMMARY OF THE INVENTION

An implant for insertion between a pair of spaced vertebrae has according to the invention a center element and a pair of end elements fitted to the center element and each adapted to engage a respective one of the vertebrae. The center and end elements have formations for varying the spacing between the end elements. According to the invention respective brackets fixed to the end elements are each fixable to the respective vertebra.

Thus it is possible to secure the implant in place by fixing its end brackets to the respective vertebrae. This leaves the center element exposed for adjustment. Thus during the operation the core assembly formed by the center and end elements can be set in place, then the end elements are secured to the respective vertebrae, and finally the center element is turned to separate the end elements and perform the desired amount of distraction of the flanking vertebrae. The brackets leave the center of the assembly completely exposed for adjustment or filling with bone fragments.

In accordance with the invention the formations includes screwthreads engaged between the center and end elements. The end elements are formed as caps engaged over ends of the center element.

According to the invention each bracket is generally L-shaped and has a long leg attached to the respective vertebrae and an arcuate short leg attached to the respective element. The long leg is also arcuate in section and each long leg is formed with at least one elongated slot. A bone screw is engaged through the slot with the respective vertebra. Furthermore each slot is formed with seats for a head of the bone screw and each short leg is formed with two holes and the respective end element is formed aligned therewith with two holes. Respective bolts each engage through a respective one of the holes of the short leg and into the respective hole of the respective end element.

Each short leg is split according to the invention between the respective holes into a pair of halves. A respective screw is engaged between each pair of halves for pulling same together and clamping the bolts in the holes of the respective end element. Each bracket is formed with a slot between the halves and with a rounded hole at an end of the slot and the long leg is formed with an elongated slot to each side of and generally parallel to the slot.

The elements are at least partially tubular and are each formed with an array of holes spaced so that the holes of the center element overlap with the holes of the end elements. This facilitates bone growth through the implant to lock it in place and in effect incorporate it in the patient's spinal column.

BRIEF DESCRIPTION OF THE DRAWING

The above and other objects, features, and advantages will become more readily apparent from the following description, reference being made to the accompanying drawing in which:

FIGS. 6, 7, and 8 are sections taken along respective lines VI—VI, VII—VII, and VIII—VIII of FIG. 4a.

SPECIFIC DESCRIPTION

Figure 1:
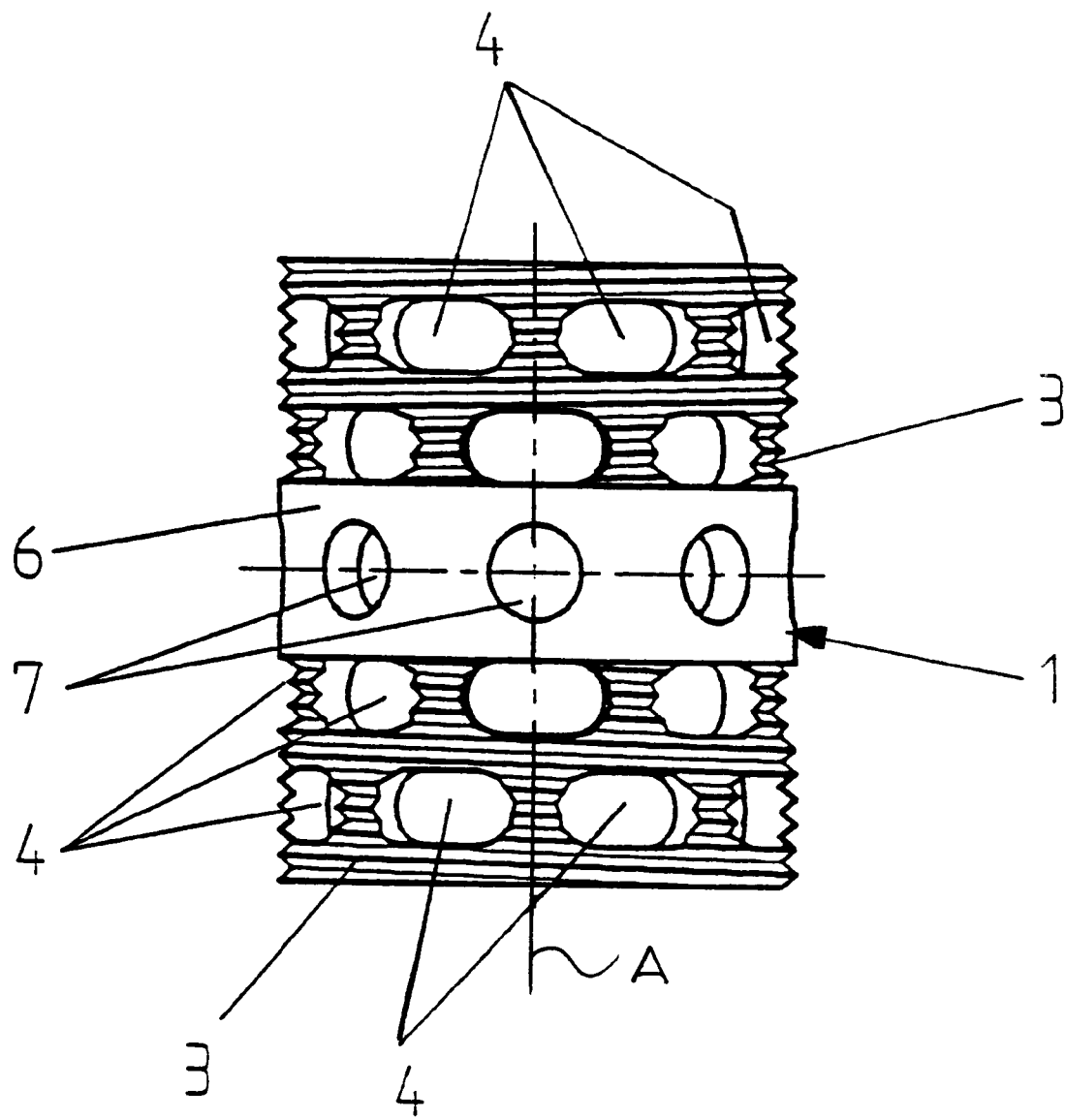
FIG. 1 is a side view of the core or center element of the implant according to the invention.
Figure 2:
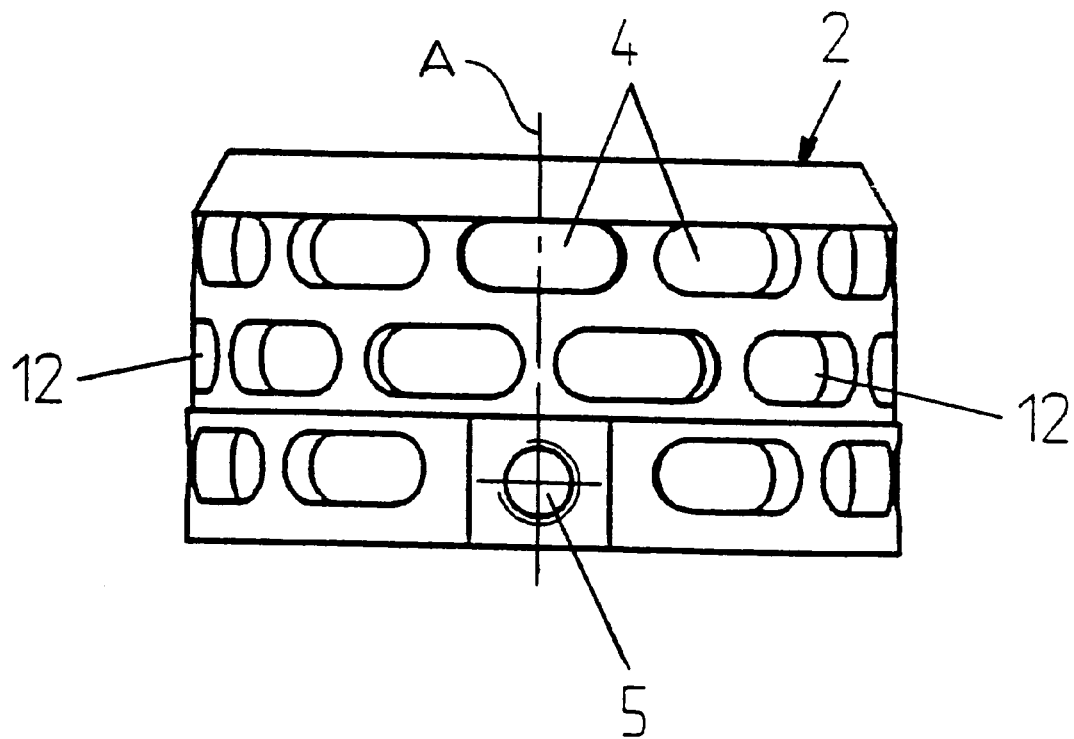
FIG. 2 is a side view of the end element or cap of the implant.
Figure 3:
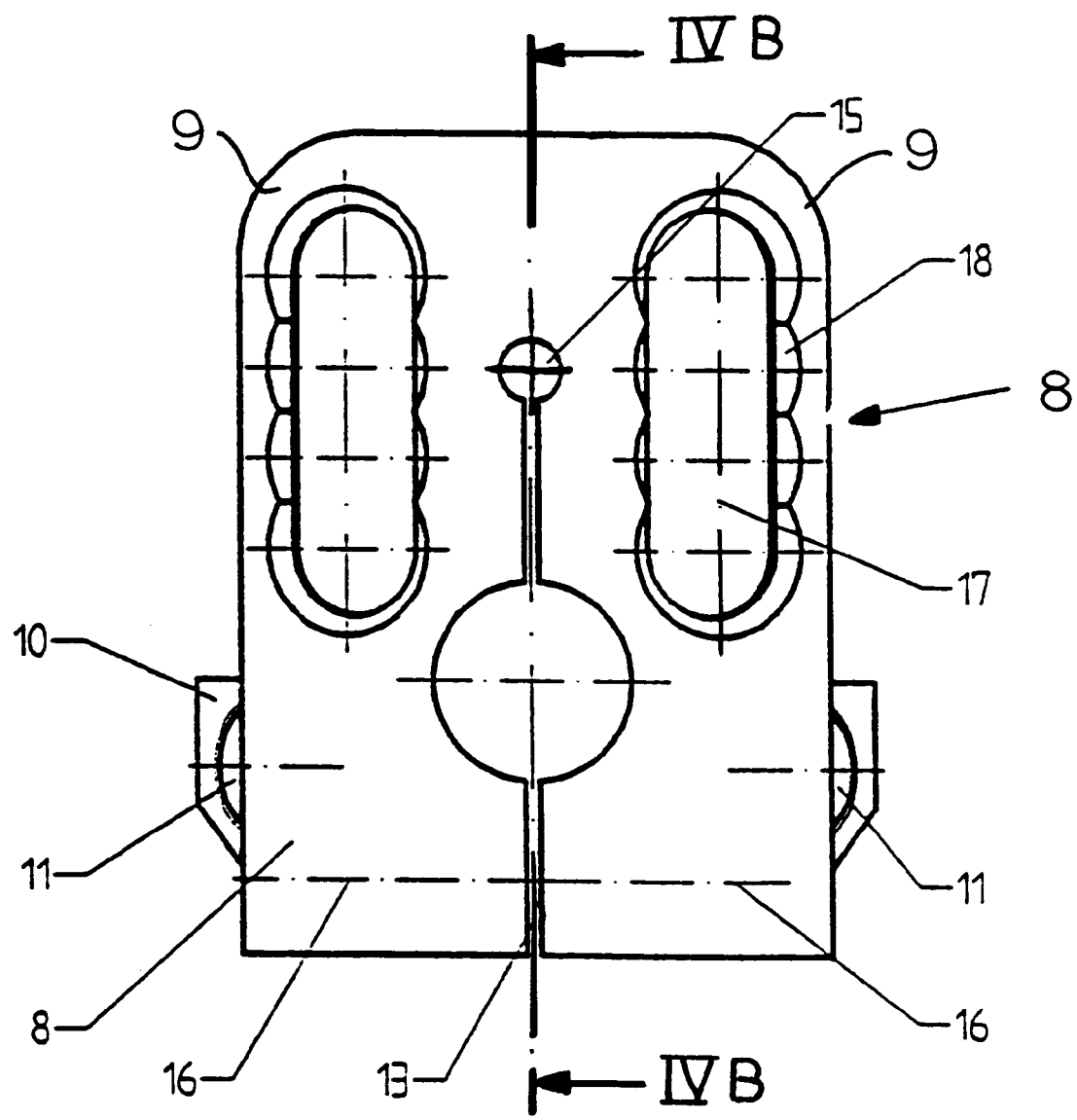
FIG. 3 is a back view of the mounting bracket for the implant of this invention.
Figure 4A:
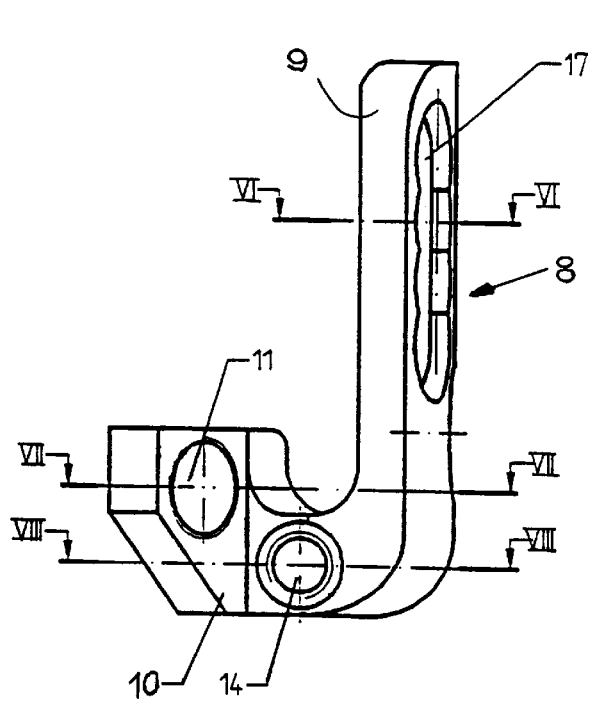
FIG. 4A is a side view of the mounting bracket.
Figure 4B:
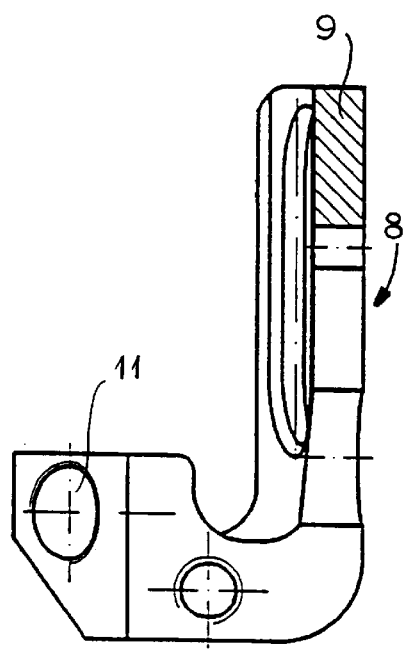
FIG. 4B is a section taken along line IVB—IVB of FIG. 3.
Figure 5:
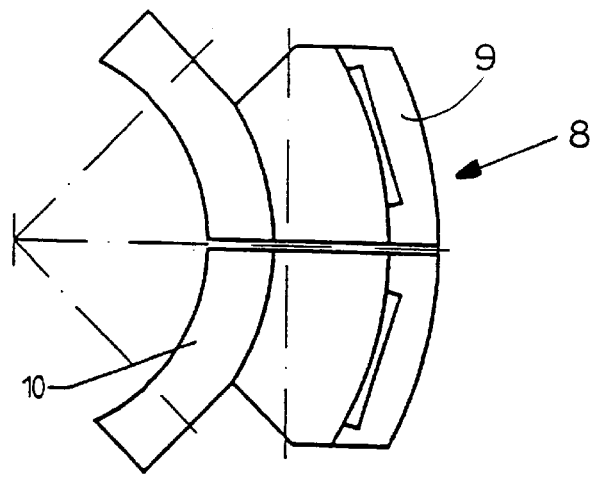
FIG. 5 is a top view of the mounting bracket.
Figure 6:
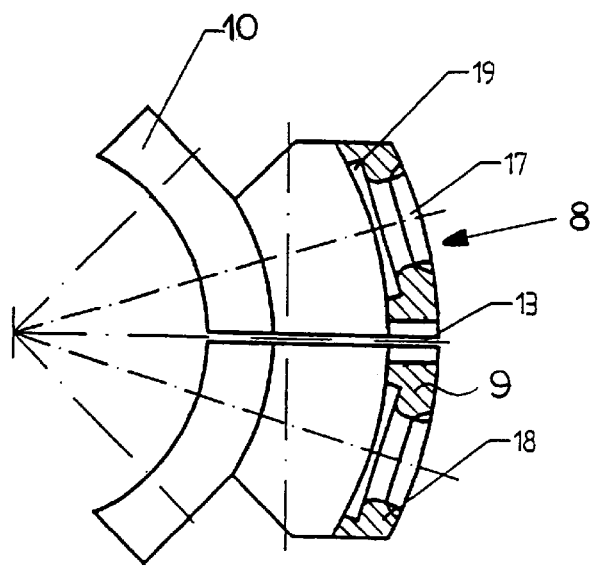
Figure 7:
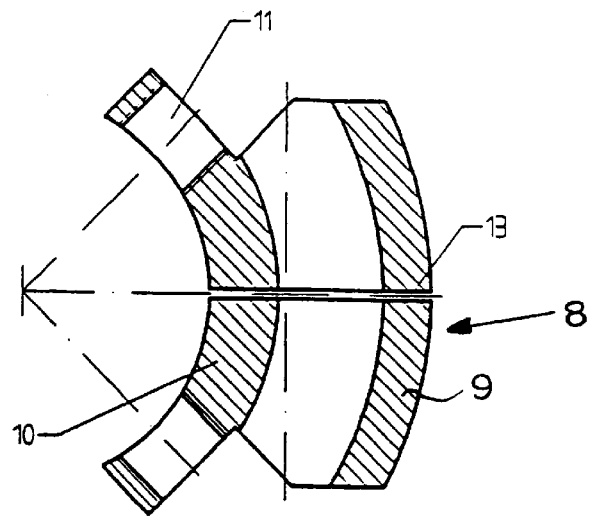
Figure 8:
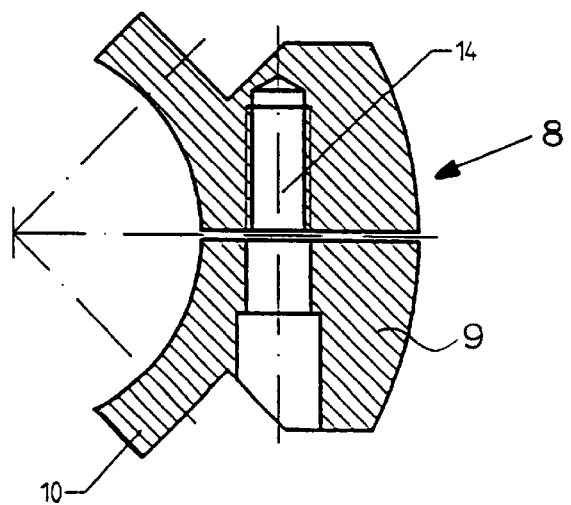

FIGS. 1 and 2 show a tubular center element 1 and an end cap or element 2 identical to those shown in above-cited U.S. Pat. No. 5,571,192. The center element 1 has upper and lower external screwthreads 3 of opposite hand that mesh when assembled with complementary internal screwthreads of the respective elements 2. The upper and lower end elements 2 are each formed at their confronting inner ends with a thickened outwardly projecting collar and at one or more locations on this collar with a thickened region which in turn is formed with a radially throughgoing threaded bore 5. A set screw can be threaded into this bore 5 to lock each of the end elements 2 on the center element 1 against relative angular movement. The center element 1 is formed with a thickened center region 6 that is clear of screwthreads and that is formed with an array of angularly equispaced and radially throughgoing circular holes or bores 7. A tool with a simple cylindrical end can be inserted into any of these holes 7 to rotate the center element 1 relative to the end elements 2 so as to increase or decrease the overall length of the implant along its axis A.

All the elements 1 and 2 are formed with arrays of radially throughgoing elongated apertures 4 that are arranged in staggered rows spaced axially by a spacing such that each of the holes 4 in an end element 2 will always overlap with at least one of the holes 4 of the element 1. As a result if the passage formed by the tubular implant is filled with bone cement and/or bone fragments before installation, good bone growth around and through this implant is insured.

Figure 9:
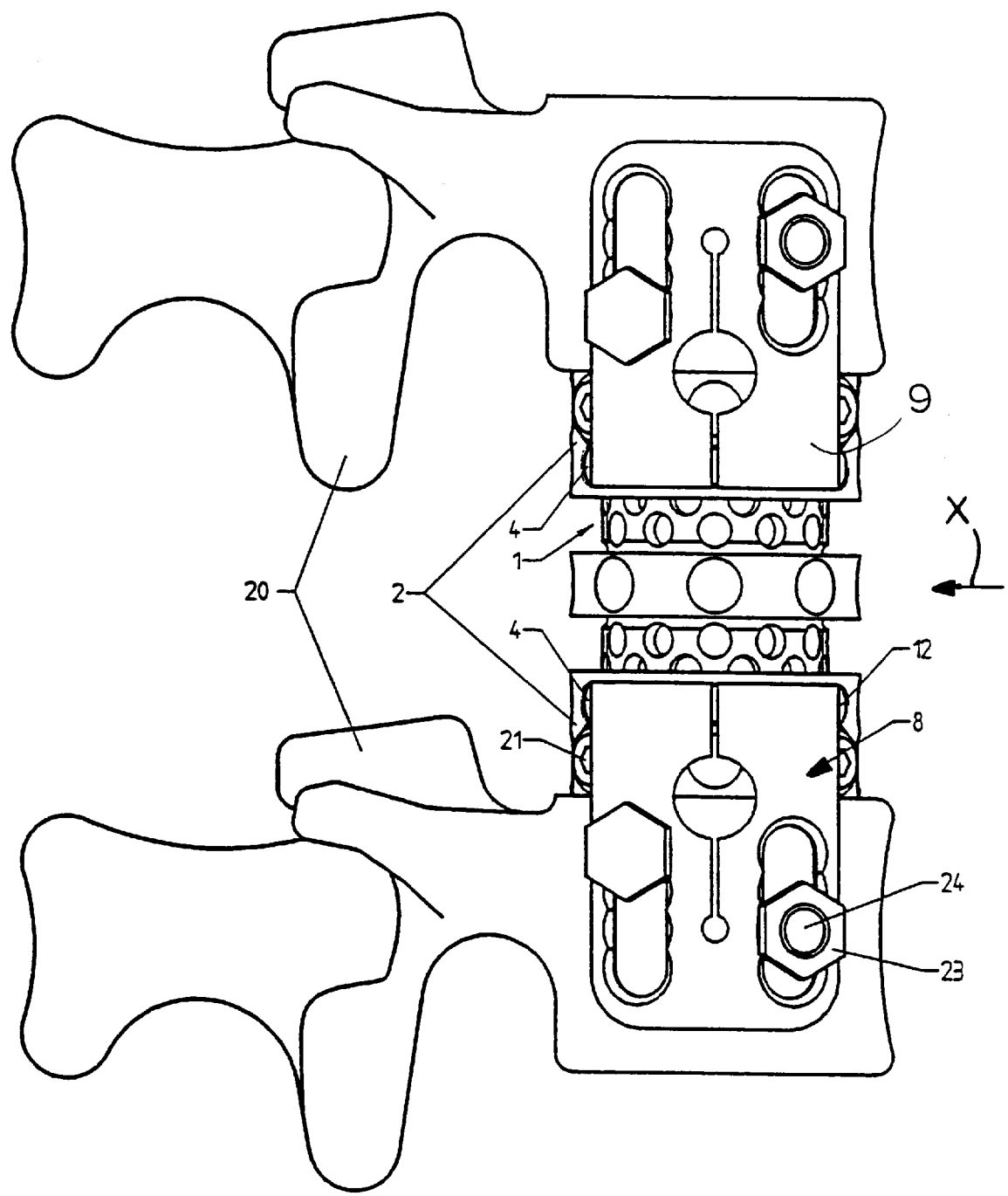
FIGS. 9 and 10 are side and back views of the implant installed in accordance with the invention in a spinal column.
Figure 10:
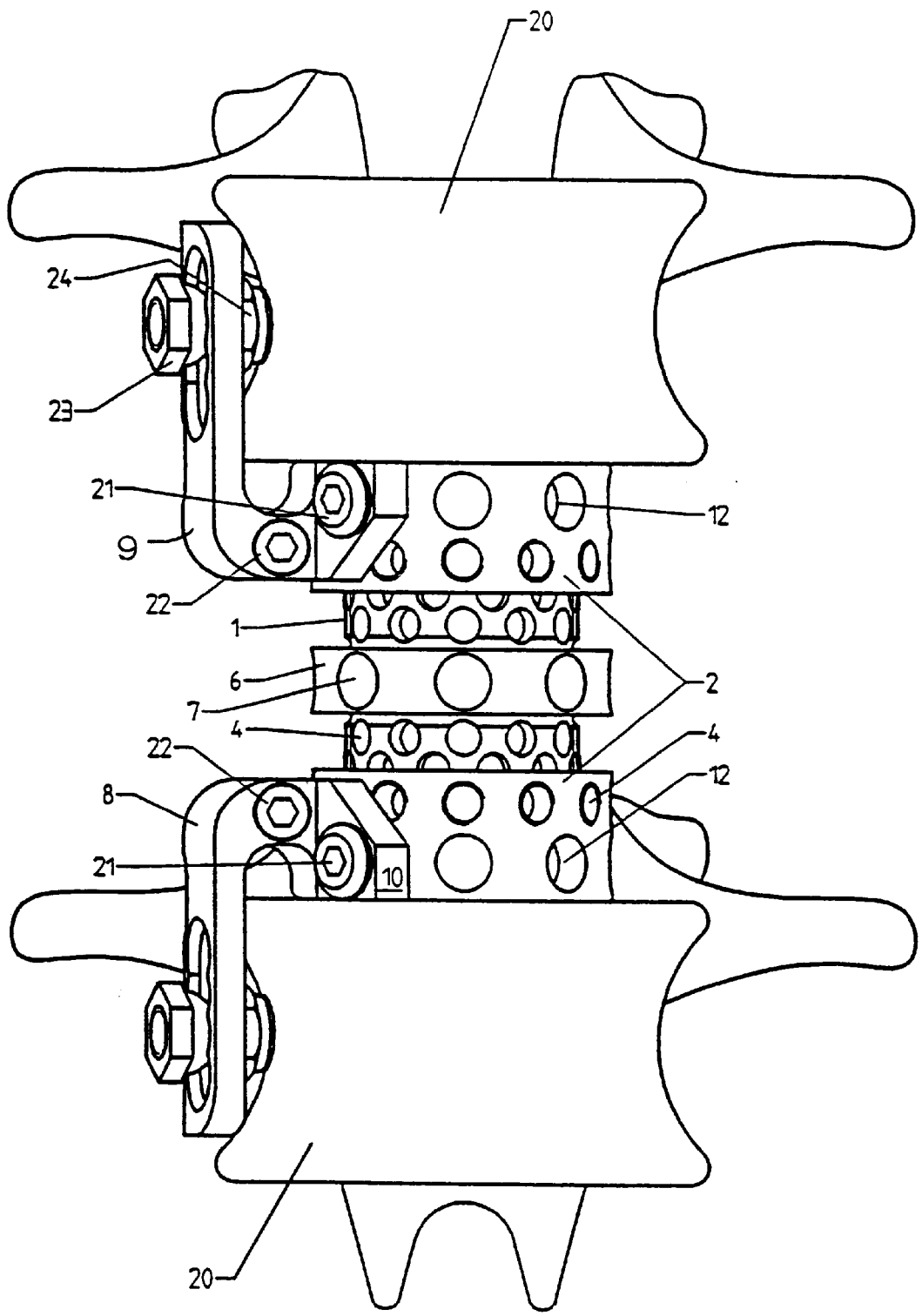

As shown in FIGS. 9 and 10, the core assembly 1, 2 of the elements 1 and 2 is fitted between a pair of vertebrae 20 and the element 1 is rotated to screw the end elements 2 apart to distract and stabilize the vertebrae 20. It is then necessary to laterally stabilize the two vertebrae 20, something done hitherto by attaching a plate or complex dorsal appliance to them.

In accordance with the invention each of the end elements 2 is secured to the respective vertebra by a respective mounting bracket 8. As shown in FIGS. 3 through 8 each such bracket 8 is basically L- or J-shaped with a long leg 9 and a short leg 10, both part-cylindrical in shape. The short leg 10 is formed with a pair of cylindrical throughgoing holes 11 centered on respective axes intended to meet in the assembled structure at the axis A and each normally receiving a bolt 21 engaged in a corresponding hole 12 of the respective end element 2.

The short leg 10 and most of the long leg 9 are formed with a longitudinal split 13 subdividing most of the bracket 8 into two halves 16. At the upper end of the split 13 the long leg 9 is formed with a circular hole 15 to allow the two halves 16 to flex relative to each other without cracking the metal of the bracket 8. A hole 14 threaded in one of the halves 16 traverses the split 13 so that a screw 22 inserted into this hole 14 can pull the two halves 16 together. Thus if two bolts 21 fitted to the holes 11 are engaged in two of the holes 12 and the screw 22 is tightened, this action will effectively lock the bracket 8 to the end element 2 by wedging the two bolts 21 against the element 2.

In addition the long leg 9 is formed with a pair of longitudinally elongated throughgoing holes or slots 17 having widened seat-forming outer edges 18 and undercut inner edges 19. Bone screws or studs 23 seated in the vertebrae 20 project through the slots, fitting to the undercut inner edges 19, and nuts 24 engaged over them and fitting in the seats 18 thus can solidly lock the brackets 8 to the vertebrae 20.

With this system it is therefore possible to solidly attach each end element 2 to the respective vertebra 20. The center element 1 is left exposed for adjustment of the distraction, and the entire assembly can, if desired, be left in place in the patient.

I claim:

1. An implant for insertion between a pair of spaced vertebrae, the implant comprising:

a center element;

a pair of end elements fitted to the center element, each formed with at least two holes, and each adapted to engage a respective one of the vertebrae, the center and end elements having formations for varying the spacing between the end elements;

respective L-shaped brackets each having an arcuate short leg fixed to a respective one of the end elements, formed with two holes generally alienable with the respective end-element holes, and each split into two halves between the respective holes and a long leg fixable to the respective vertebra;

respective bolts each engaging through a respective one of the short-leg holes and into the respective end-element hole; and respective screws engageable between the halves for pulling same together and clamping the bolts in the respective end-element holes.

2. The vertebral implant defined in claim 1 wherein the formations include screwthreads engaged between the center and end elements, the end elements being formed as caps engaged over ends of the center element.

3. The vertebral implant defined in claim 1 wherein the long leg is also arcuate in section.

4. The vertebral implant defined in claim 1 wherein each long leg is formed with at least one elongated slot, the implant further comprising a bone screw engageable through the slot with the respective vertebra.

5. The vertebral implant defined in claim 4 wherein each slot is formed with seats for a head of the bone screw.

6. The vertebral implant defined in claim 1 wherein each bracket is formed with a slot between the halves and with a rounded hole at an end of the slot.

7. The vertebral implant defined in claim 6 wherein the long leg is formed with an elongated slot to each side of and generally parallel to the slot.

8. The vertebral implant defined in claim 1 wherein the elements are at least partially tubular and are each formed with an array of holes spaced so that the holes of the center element overlap with the holes of the end elements.

* * * * *